US009095551B2

(12) United States Patent
Ushida et al.

(10) Patent No.: US 9,095,551 B2
(45) Date of Patent: Aug. 4, 2015

(54) COMBINED PREPARATION FOR TREATING JOINT DISEASES

(75) Inventors: Kiminori Ushida, Wako (JP); Koji Kihira, Wako (JP); Takayuki Baba, Wako (JP); Kayoko Taniguchi, Wako (JP); Makoto Urai, Wako (JP); Masato Sato, Isehara (JP); Naoshi Ohta, Isehara (JP); Joji Mochida, Isehara (JP)

(73) Assignees: RIKEN, Wako-shi (JP); TOKAI UNIVERSITY EDUCATIONAL SYSTEM, Tokyo (JP)

( * ) Notice: Subject to any disclaimer, the term of this patent is extended or adjusted under 35 U.S.C. 154(b) by 0 days.

(21) Appl. No.: 13/147,090

(22) PCT Filed: Jan. 29, 2010

(86) PCT No.: PCT/JP2010/051658
§ 371 (c)(1),
(2), (4) Date: Jul. 29, 2011

(87) PCT Pub. No.: WO2010/087521
PCT Pub. Date: Aug. 5, 2010

(65) Prior Publication Data
US 2012/0135934 A1    May 31, 2012

(30) Foreign Application Priority Data
Jan. 29, 2009   (JP) .................................. 2009-018719

(51) Int. Cl.
*A61P 19/02*    (2006.01)
*A61K 38/16*    (2006.01)
*A61K 31/728*    (2006.01)
*A61K 38/17*    (2006.01)

(52) U.S. Cl.
CPC ........... *A61K 38/1735* (2013.01); *A61K 31/728* (2013.01)

(58) Field of Classification Search
None
See application file for complete search history.

(56) References Cited

U.S. PATENT DOCUMENTS

| | | | | |
|---|---|---|---|---|
| 6,743,774 | B1 * | 6/2004 | Jay .............................. | 514/16.7 |
| 7,829,679 | B2 * | 11/2010 | Ushida et al. ................. | 530/395 |
| 2010/0151514 | A1 | 6/2010 | Ushida et al. | |
| 2010/0234322 | A1 | 9/2010 | Asari | |

FOREIGN PATENT DOCUMENTS

| | | |
|---|---|---|
| EP | 1 947 111 A1 | 7/2008 |
| JP | 2003 500022 | 1/2003 |
| JP | 2004-230184 | 8/2004 |
| JP | 2005-144131 | 6/2005 |
| WO | WO 98/10783 | 3/1998 |
| WO | 2007 020889 | 2/2007 |
| WO | WO2007/020889 | * 2/2007 |
| WO | 2008 068854 | 6/2008 |

OTHER PUBLICATIONS

Goto et al., Olin. Exp. Rheumatol., 2001, vol. 19(4):377-383.*
Jay, G.D., et al., "The role of lubricin in the mechanical behavior of synovial fluid," Proc. Natl. Acad. Sci., vol. 104, No. 15, pp. 6194-6199, (Apr. 10, 2007).
International Search Report issued Mar. 16, 2010 in PCT/JP10/051658 filed Jan. 29, 2010.
M. Reijman et al.,—"Is There an Association Between the Use of Different Types of Nonsteroidal Antiinflammatory Drugs and Radiologic Progression of Osteoarthritis?", Arthritis & Rheumatism, vol. 52, No. 10, Oct. 2005, pp. 3137-3142.
Robert John Petrella et al.,—"Effects of Hyaluronate Sodium on Pain and Physical Functioning in Osteoarthritis of the Knee", Arch Intern Med, vol. 162, Feb. 11, 2002, pp. 292-298.
M. Dougados et al.,—"High molecular weight sodium hyaluronate (hyalectin) in osteoarthritis of the knee: a 1 year placebo-controlled trial", Osteoarthritis Cartilage, Apr. 1993 1(2): 97-103, internet article (abstract only).
Robert S. Salk et al.,—"Sodium Hyaluronate in the Treatment of Osteoarthritis of the Ankle: A Controlled, Randomized, Double-Blind Pilot Study", The Journal of Bone and Joint Surgery, vol. 88-A, No. 2, Feb. 2006, pp. 295-302.
M. Goto et al.,—"Intra-articular injection of hyaluronate (SI-6601D) improves joint pain and synovial fluid prostaglandin E2 levels in rheumatoid arthritis: A multicenter clinical trial", Clinical and Experimental Rheumatology, 2001, 19, pp. 377-383.
David K. Rhee et al.,—"The secreted glycoprotein lubricin protects cartilage surfaces and inhibits synovial cell overgrowth", The Journal of Clinical Investigation, vol. 115, No. 3, Mar. 2005, pp. 622-631.
G.D. Jay et al., "The role of lubricin in the mechanical behavior of synovial fluid", PNAS, Apr. 10, 2007, vol. 104, No. 15, pp. 6194-6199.
Debby P. Chang et al.,—"Conformational Mechanics, Adsorption, and Normal Force Interactions of Lubricin and Hyaluronic Acid on Model Surfaces", Langmuir 2008, vol. 24, No. 4, pp. 1183-1193.
C.R. Flannery et al.,—"Intraarticular Lubricin Supplementation is Chondroprotective and Prevents Cartilage Degeneration in Experimental Osteoarthritis", Podium Presentations, S19, 2008.
M.A. Rivera-Bermudez et al.,—Pharmacokinetic Analysis of Recombinant Lubricin Following Intra-Articular Supplementation in Rat Knee Joints, Osteoarthritis and Cartilage, vol. 16, Supplement 4, S46, 2008.
Akiko Masuda et al., "Mucin (Qniumucin), a Glycoprotein from Jellyfish and Determination of its Main Chain Structure", J. Nat. Prod. 2007, 70, pp. 1089-1092.

(Continued)

*Primary Examiner* — Xiaozhen Xie
(74) *Attorney, Agent, or Firm* — Oblon, McClelland, Maier & Neustadt, L.L.P.

(57) ABSTRACT

An object of the present invention is to enable the repair and regeneration of articular cartilage, which could not be achieved by conventional therapies, and to provide a safe and inexpensive agent that is effective for the treatment of joint diseases such as osteoarthritis. According to the present invention, a combined formulation for simultaneously, separately, or sequentially administering a hyaluronic acid and an animal mucin-type glycoprotein for the treatment of joint diseases is provided.

10 Claims, 6 Drawing Sheets

(56) References Cited

OTHER PUBLICATIONS

Esmeralda N. Blaney Davidson et al., "Elevated extracellular matrix production and degradation upon bone morphogenetic protein-2 (BMP-2) stimulation point toward a role for BMP-2 in cartilage repair and remodeling", Arthritis Research & Therapy, 2007, pp. 1-11 (internet article), vol. 9, No. 5.

Combined Taiwanese Office Action and Search Report issued Apr. 17, 2014, in Taiwanese Patent Application No. 099102703 with English Translation of category of cited documents.

I Uthman, et al., "Intra-articular therapy in osteoarthritis", Postgraduate Medical Journal, 79, 2003, 1 cover page, pp. 449-453.

Luis A. Solchaga, et al., Hyaluronic Acid-Based Polymers as Cell Carriers for Tissue-Engineered Repair of Bone and Cartilage, Journal of Orthopaedic Reseach, vol. 17, No. 2, 1999, pp. 205-213.

Office Action issued Jul. 28, 2014 in Taiwanese Patent Application No. 099102703 issued.

Michael V. Volin, et al., "Expression of Mucin 3 and Mucin 5 AC in Arthritic Synovial Tissue", Arthritis & Rheumatism, vol. 58, No. 1, Jan. 2008, pp. 46-52.

* cited by examiner

H-E staining

Toluidine blue staining

Group A

Group B

Group C

Group D

Fig. 6

SEQUENCE LISTING

```
<160> NUMBER OF SEQ ID NOS: 1

<210> SEQ ID NO 1
<211> LENGTH: 8
<212> TYPE: PRT
<213> ORGANISM: Aurelia aurita
<220> FEATURE:
<223> OTHER INFORMATION: May also be derived from Chrysaora melanaster
<220> FEATURE:
<221> NAME/KEY: MOD_RES
<222> LOCATION: (2)..(2)
<223> OTHER INFORMATION: Val or Ile

<400> SEQUENCE: 1

Val Xaa Glu Thr Thr Ala Ala Pro
1               5
```

COMBINED PREPARATION FOR TREATING JOINT DISEASES

CROSS-REFERENCE TO RELATED APPLICATIONS

The present application is a 35 U.S.C. §371 National Stage patent application of International patent application PCT/JP2010/051658, filed on Jan. 29, 2010, which claims priority to Japanese patent application JP 2009-018719, filed on Jan. 29, 2009.

TECHNICAL FIELD

The present invention relates to a combined formulation of a hyaluronic acid and an animal mucin-type protein, which can be used for treatment of joint diseases such as osteoarthritis.

BACKGROUND ART

Many failures elicited at human and mammalian joints due to diseases, aging, or the overuse of joints exhibit degeneration of synovial fluid, or damage generated on the cartilage surfaces. These failures reduce the essential function of joint; that is, the ability to realize smooth skeletal motion with low friction, and result in disorders, pain or the like in bodies. For example, osteoarthritis (hereinafter referred to as "OA") is one of the most common joint diseases and is said to be developed in 25% or more of people aged 60 or older. OA is characterized by cartilage degeneration (retrogressive degeneration) which gradually progresses over a long period of time. OA occurs mainly in weight-bearing joints of lower extremities, such as knee joints or hip joints. The onset of OA is strongly correlated with age. Therefore, OA is one of major causes of pain and joint dysfunction in the elderly.

The maintenance of osteochondral functions is an important factor in maintaining ADL (activity of daily life) of the elderly at a high level. It is also an industrial demand because of the societal demand for promoting social activity and economic activity of people in the aging society. Factors that contribute to the onset include family history of OA, previous damage to joint due to trauma or surgery, and the age of joint (i.e., the abrasion and laceration of the articulating surface of joint). OA is very common among the elderly as described above, and it can also be developed even in children, after trauma such as fractures, anterior cruciate ligament injuries or meniscal injuries, or when having an underlying disease such as haemophilia. Currently, medication for OA is performed mainly for the purpose of pain relief, and is composed of systemic analgesic therapy and local intraarticular treatment. For the systemic analgesic therapy, non-steroidal anti-inflammatory drugs (NSAIDs) are broadly used [Arthritis Rheum 43: 1905-1915 (2000)]. However, some articles point out that NSAIDs can accelerate the progression of pathological conditions [Huskisson, E. C. et al, J. Rheumatol 22: 1941-1946 (1995); Rashad, S. et al., Lancet 2: 519-522 (1989); Dougados, M. et al., Ann. Rheum. Dis. 55: 356-362 (1996)]. Meanwhile, for the local intraarticular treatment, hyaluronic acid injection therapy is widely known.

A method in which the viscosity of synovial fluid is increased by adding an agent from the outside to alleviate the cause of physical damage to a joint, as in the case of the hyaluronic acid injection therapy, is called viscosupplementation (patent document 1). The viscosupplementation is widely used not only for treatment of the above OA, but also for cases in which superficial defects are considered to occur as a result of frequent interaction between cartilages resulting from lowered synovial fluid due to aging or diseases. A hyaluronic acid or a derivative thereof is often used for the viscosupplementation, and effects of increasing synovial fluid viscosity and suppressing the destruction of articular cartilage have been observed (non-patent documents 1-4). Also, the anti-inflammatory action of hyaluronic acid is said to be effective in alleviating diseases (non-patent document 5). However, the viscosupplementation using a hyaluronic acid does not have a significant action of repairing superficial defects in many cases, and thus the use thereof is limited only for temporal palliative therapy. Further, since the hyaluronic acid administered is metabolized and consumed within several weeks, this treatment must be employed repeatedly in order to maintain effects and alleviate symptoms.

Meanwhile, a therapy called tribosupplementation has also been proposed, which supplements not synovial fluid viscosity but a boundary lubricating substance near the synovial membrane. For example, when tribonectin, which is a mucin-type glycoprotein, is directly administered, the tribosupplementation effect is expected (patent document 1). Further, in recent years, a glycoprotein having a mucin region called lubricin, which is included in tribonectin, has been identified in synovial fluid and on joint surfaces, and it has also been reported to contribute to tribosupplementation for joints (non-patent documents 6 and 7). Lubricin is characterized in that it has, between non-mucin-type sequences on both ends, a mucin-type sequence region in which O-linked sugar chains are bound to the protein backbone. A hypothesis has been proposed that the non-mucin-type sequences have affinity for and interact with cartilage surfaces, so as to settle lubricin thereon (non-patent document 8). When lubricin is settled on a cartilage surface, the mucin region and non-mucin region are thought to function separately, such that the mucin region plays the role of reducing friction by externally positioning sugar chains like a bristle brush, and the non-mucin region plays the role of accelerating settlement on a cartilage surface. This is called a brushing model based on its shape. On the other hand, no such mechanism has been proposed for the aforementioned tribonectin. However, tribonectin also has a mucin-type sequence that reduces friction and a non-mucin region, which is a common feature shared by lubricin and tribonectin. It is similarly considered that the effect of reducing friction is obtained through dense (probably in a film-form) adsorption of the mucin region to a cartilage tissue surface. Therefore, like the case of these 2 types of mucin-type glycoproteins, it can be said that mucin-type sugar chain moiety for friction reduction and a non-mucin region for adsorption to a cartilage surface are essential (non-patent document 8).

As described above, it is expected that a mucin-type glycoprotein can be injected into articular tissue for the purpose of tribosupplementation and then used for treatment of joint diseases. However, it is very difficult to artificially prepare an entirely identical glycoprotein by binding sugar chains moiety, although its backbone peptide portion can be synthesized upon production of a mucin-type glycoprotein. This is because binding of sugar chains via O-glycoside bonds (O-glycosylation) is a synthetic pathway performed by a post-translational modification reaction in vivo, and is a biological reaction that cannot be easily controlled. Although it may not be impossible to bind sugar chains having O-glycoside bonds by expression using a special cell line, an enzyme reaction, a precise organic chemical reaction, or the like, it would be impossible to introduce sugar chains at sufficient densities or conversion rates, or it would require enormous expenses for the realization. Therefore, since the sufficient supply of a mucin-type glycoprotein cannot be ensured, the above therapy using such a glycoprotein cannot practically be employed, and thus the spread and penetration thereof are difficult.

Recently, the artificial synthesis of a mucin-type glycoprotein as a simplified compound has been attempted. For example, it has been reported that a mucin-type glycoprotein having a shortened mucin sequence portion of lubricin could be synthesized and settled on a joint surface, although the therapeutic effect has not been confirmed (non-patent documents 9 and 10).

Mucin-type glycoproteins are broadly distributed as mucus components among general animals and plants. Many of plant mucin-type glycoproteins have structures wherein short peptides bind to long sugar chains, whereas animal mucin-type glycoproteins are characterized by quite long peptide chains, and the core peptide sequence, sugar chain structure, non-mucin-type domain, and the like greatly vary depending on animal type. Various animal mucin-type glycoproteins (animal mucins) are known to date. Although such mucins are mainly from the digestive juice or saliva of a domestic animal such as cattle, the presence of mucin-type glycoproteins in snails, starfishes, and cuttlefishes has also been reported. However, all of these animal mucins have problems in that: they cannot be supplied in large quantities because the production amounts are limited; their safety is poor because of low purity; and structural analyses (peptide chain sequence analysis and sugar chain sequence analysis) have not been sufficiently conducted. By contrast, mucin (qniumucin) that has been collected from jellyfish in recent years is characterized in that it has a simple structure, is almost purely composed of an mucin sequence region, and can be produced at low cost in large quantities. Thus, the effective use of qniumucin is expected (non-patent document 11 and patent document 2).

Besides the above hyaluronic acid and mucins, a technique of administering a tissue growth factor has also been proposed (patent document 3, patent document 4, and non-patent document 12). However, although effects such as inhibition of the progression of damage and alleviation of pain are exerted by the technique as in those of conventional therapies, the effect of accelerating self-repairing action on damage has not been obtained.

(Patent document 1) JP Patent Publication (Kohyo) No. 2003-500022
(Patent document 2) WO 2007/020889
(Patent document 3) JP Patent Publication (Kokai) No. 2004-230184
(Patent document 4) JP Patent Publication (Kokai) No. 2005-144131
(Non-patent document 1) Reijman, M. et al., Arthritis Rheum 52: 3137-3142 (2005)
(Non-patent document 2) Petrella, R. J., DiSilvestro, M. D., Arch Intern Med. 162: 292-298 (2002)
(Non-patent document 3) Dougados, M. et al, Osteoarthritis Cartilage 1: 97-103 (1993)
(Non-patent document 4) Salk, R. S. et al., J. Bone Joint Surg. Am. 88: 295-302 (2006)
(Non-patent document 5) Goto M., Clin. Exp. Rheumatol. 19:327-383 (2001)
(Non-patent document 6) Rhee D. K. et al., J. Clin. Invest. 115: 622-631 (2005)
(Non-patent document 7) Jay, G. D. et al., Proc Natl Acad. Sci. 104: 6194-6199 (2007)
(Non-patent document 8) Chang D. P. et al., Langmuir 24: 1183-1193 (2008)
(Non-patent document 9) Flannery, C. R. et al., Osteoarthritis and Cartilage, 15, S19 (2008)
(Non-patent document 10) Rivers-Bermudez, M. A. et al., Osteoarthritis and Cartilage, 15, S43 (2008)
(Non-patent document 11) Masuda A. et al., J. Nat. Prod. 70(7):1089-1092 (2007)
(Non-patent document 12) Davidson, E. N. B. et al., Arthritis Research & Therapy 9:R102 (2007)

DISCLOSURE OF THE INVENTION

As described above, various methods have been proposed for the purpose of treating joint diseases such as osteoarthritis or alleviating the symptoms. However, viscosupplementation alone has no effect of repairing articular cartilages, and tribosupplementation cannot be used for practical treatment because it is currently difficult to artificially produce in large quantities a mucin-type glycoprotein having a structure that can be used for tribosupplementation.

Therefore, an object of the present invention is to enable repair and regeneration of articular cartilages, which cannot be achieved by conventional therapies, and to provide a safe and inexpensive agent that is effective for treatment of joint diseases such as osteoarthritis.

As a result of intensive studies to achieve the above object, the present inventors have found that when an animal mucin-type glycoprotein is used in combination with a hyaluronic acid which has been conventionally used for viscosupplementation for joints, effects of repairing and regenerating articular cartilage that cannot be achieved by conventional therapies are synergistically elicited. Thus, the present inventors have completed the present invention.

The present invention encompasses the following (1) to (12).

(1) A combined formulation for simultaneously, separately, or sequentially administering a hyaluronic acid and an animal mucin-type glycoprotein for treatment of joint diseases.

(2) The combined formulation according to (1), wherein 95% or more of the full-length amino acid sequence of the animal mucin-type glycoprotein is composed of a mucin region.

(3) The combined formulation according to (1), wherein: the animal mucin-type glycoprotein has a repeat structure that comprises 3 to 2000 repeating units, wherein each repeating unit consists of the amino acid sequence represented by the following formula (I) (SEQ ID NO: 1):

Val-Xaa-Glu-Thr-Thr-Ala-Ala-Pro  (I)

(wherein Xaa denotes Val or Ile); and sugar chains are bound to 50% or more of all Thr residues in the repeat structure.

(4) The combined formulation according to (1), wherein the animal mucin-type glycoprotein is an extract from jellyfish.

(5) The combined formulation according to any one of (1) to (4), wherein the hyaluronic acid and the animal mucin-type glycoprotein are contained in separate formulations or in the same formulation.

(6) The combined formulation according to any one of (1) to (5), which is an injectable formulation.

(7) The combined formulation according to any one of (1) to (6), wherein the treatment of joint diseases is the repair and regeneration of articular cartilage.

(8) A method for treating joint diseases, comprising administering a hyaluronic acid and an animal mucin-type glycoprotein in combination.

(9) The method according to (8), wherein 95% or more of the full-length amino acid sequence of the animal mucin-type glycoprotein is composed of a mucin region.
(10) The method according to (8), wherein:
the animal mucin-type glycoprotein has a repeat structure that comprises 3 to 2000 repeating units, wherein each repeating unit consists of the amino acid sequence represented by the following formula (I) (SEQ ID NO: 1):

Val-Xaa-Glu-Thr-Thr-Ala-Ala-Pro    (I)

(wherein Xaa denotes Val or Ile); and
sugar chains are bound to 50% or more of all Thr residues in the repeat structure.
(11) The method according to (8), wherein the animal mucin-type glycoprotein is an extract from jellyfish.
(12) The method according to any one of (8) to (11), wherein the treatment of joint diseases is the repair and regeneration of articular cartilage.

EFFECTS OF THE INVENTION

The combined formulation of the present invention comprising a hyaluronic acid and an animal mucin-type glycoprotein enables the repair and regeneration of articular cartilages, which have poor self-curing ability, and for which it has been thought that it is almost impossible to repair or regenerate them once they are damaged. Thus, new and synergistic therapeutic effects can be obtained, unlike those of conventional agents for treating joint diseases intended for viscosupplementation or tribosupplementation. Further, the animal mucin-type glycoprotein contained in the combined formulation of the present invention has short sugar chains, contains few types of constituent sugar, contains almost no sialic acid, and does not have a non-mucin region which is observed in lubricin or tribonectin, so that the biological reactions such as immunity or allergy are relatively mild and thus it is excellently safe.

BRIEF DESCRIPTION OF THE DRAWINGS

FIG. 6 shows the results of evaluation of the degree of cartilage degeneration based on OA score in an anterior cruciate ligament transection OA model (week 10 after surgery) to which predetermined agents were administered (group A: the physiological saline (control) group; group B: the group to which a hyaluronic acid was administered alone; group C1: the group to which Nomura's jellyfish-derived mucin extract was administered alone; group C2: the group to which a moon jelly-derived mucin extract was administered alone; group D1: the group to which a combination of Nomura's jellyfish-derived mucin extract+a hyaluronic acid was administered; group D2: the group to which a combination of moon jelly-derived mucin extract+a hyaluronic acid was administered. Column and longitudinal line: average and standard deviation for each group).

This application claims priority to Japanese patent application No. 2009-018719 filed on Jan. 29, 2009, and the contents of the patent application are herein incorporated by reference.

BEST MODE FOR CARRYING OUT THE INVENTION

The present invention will be explained in detail as follows.
The present invention relates to a combined formulation for simultaneously, separately, or sequentially administering a hyaluronic acid and an animal mucin-type glycoprotein in treatment of joint diseases.

The hyaluronic acid to be used in the present invention may be originated from any source and produced by any method, as long as it is a hyaluronic acid usually used for intraarticular viscosupplementation. The molecular weight of the hyaluronic acid preferably ranges from about 500,000 to 20,000,000, and more preferably ranges from about 800,000 to 2,000,000. Further, the hyaluronic acid as used herein also includes its alkali metal salts, such as sodium salt, potassium salt, and lithium salt.

In the present invention, an animal mucin-type glycoprotein to be used in combination with a hyaluronic acid is substantially composed of a mucin region and preferably does not have a non-mucin region which is observed in lubricin or tribonectin, or has quite few non-mucin regions.

The above expression, "substantially composed of a mucin region" specifically means that 95% or more, preferably 98% or more, and more preferably 100% of the full-length amino acid sequence is composed of a mucin region. As used herein, the term "mucin-type glycoprotein (mucin)" refers to a glycoprotein that is a major component of mucus, and that is a macromolecular substance in which sugar chains (mucin-type sugar chains) are bound in a branched manner via O-glycoside bonds to threonine (Thr) and/or serine (Ser) of a protein (a peptide chain) which is composed of amino acids being connected with each other. Further, the above term "mucin region" refers to a region in which mucin-type sugar chains are densely present, and that has a structure wherein an amino acid sequence that consists of several amino acid residues including an amino acid residue having a mucin-type sugar chain being bound is repeated (mucin-type sequence). For example, in the case of a mucin-type glycoprotein having a repeat sequence of consecutive amino acid sequences of about 10 residues as described below, a region can be determined to be a mucin region by confirming that, a mucin-type sugar chain is bound to at least one amino acid residue among about 10 amino acid residues that constitutes an amino acid sequence selected at random from the entire amino acid sequence that constitutes the mucin-type glycoprotein. Further, the above "non-mucin region" refers to a region other than "mucin region", that is, a region lacking a mucin-type sugar chain or having extremely few mucin-type sugar chains, and having an amino acid sequence consisting of amino acid residues to which no mucin-type sugar chain is bound (non-mucin-type sequence). For example, in the case of a mucin-type glycoprotein having a repeat sequence of consecutive amino acid sequences of about 10 residues as described below, a region can be determined to be a non-mucin region by confirming that, a mucin-type sugar chain is not bound to any of about 10 amino acid residues that constitutes an amino acid sequence selected at random from the entire amino acid sequence that constitutes the mucin-type glycoprotein.

In the animal mucin-type glycoprotein in the present invention, although the sugar chain structure and composition of a mucin-type sugar chain that are bound to an amino acid residue are not particularly limited, it is preferable that the sugar chain is short (short sugar chain consisting of 1 saccharide or 2 saccharides) and the types of constituent sugars are few. Further, although the types of amino acid residue to which sugar chains are bound are not particularly limited, it is preferable that sugar chains are bound to threonine residues (Thr) and/or serine residues (Ser).

Examples of such an animal mucin-type glycoprotein include a mucin-type glycoprotein having a repeat sequence of consecutive amino acid sequences of about 10 residues which are called tandem repeats, preferably a mucin-type glycoprotein having a repeat structure that comprises 3 or more repeating units, wherein each repeating unit consists of the amino acid sequence represented by the following formula (I) (SEQ ID NO: 1):

Val-Xaa-Glu-Thr-Thr-Ala-Ala-Pro  (I)

(wherein Xaa denotes Val or Ile) disclosed in WO 2007/020889. The number of repetition of the above unit ranges from 3 to 2000, and preferably ranges from 3 to 700. The molecular weight of the mucin-type glycoprotein is widely distributed having a peak at about 10 to 100 kDa, but a mucin-type glycoprotein having any molecular weight may be used in the present invention.

The above repeating units may be directly connected or connected via linkers. Examples of the linker include, but are not limited to, S—S bond which uses cysteine.

Further, in the animal mucin-type glycoprotein having a repeat structure that comprises the repeating unit of formula (I) above, Thr residues to which sugar chains are bound account for 50% or more, preferably 70% or more, and more preferably 80% or more of all Thr residues in the above repeat structure.

In addition, in the animal mucin-type glycoprotein in the present invention, monosaccharides constituting a sugar chain are not particularly limited, as long as they are monosaccharides found in general mucin-type glycoproteins. Examples of such a monosaccharide include N-acetylgalactosamine, galactose, N-acetylglucosamine, sialic acid, arabinose, and fucose. In particular, a sugar chain composed of N-acetylgalactosamine and/or galactose is preferable. Specifically, it is preferable that N-acetylgalactosamine and galactose are bound to a threonine residue (Thr) in the above repeating unit to form the structure of Thr-GalNAc-Gal, or N-acetylgalactosamine alone is bound to the same to form the structure of Thr-GalNAc.

Further, a jellyfish-derived extract may be used as the animal mucin-type glycoprotein of the present invention. A jellyfish whose safety for humans or animals has been confirmed is preferable. Examples thereof include moon jelly, Nomura's jellyfish, and edible jellyfish (*Rhopilema esculenta*). Further, portions of jellyfish from which the mucin-type glycoprotein is extracted are not particularly limited. For example, outer mesoglea, oral arm, gastric corpus, body fluid, and the like, or liquid components obtained via cryopreservation or preservation at normal temperature can be used. A method for obtaining an extract containing the mucin-type glycoprotein using these jellyfish portions as materials, and a method for purifying the thus obtained extract using means that are generally employed for protein purification such as liquid chromatography may be performed in accordance with WO 2007/020889.

Although the jellyfish extract to be used in the present invention is preferably a jellyfish extract highly purified to contain the above animal mucin-type glycoprotein accounting for 90% or more of the extract, it may be a crudely purified extract (crudely purified mucin) containing the animal mucin-type glycoprotein accounting for about 50% of the extract in view of cost reduction and efficiency. For example, one can use a jellyfish extract immediately before purification obtained according to the method described in the above-mentioned publication as the crudely purified extract.

Upon the use of the combined formulation of the present invention, the above animal mucin-type glycoprotein and the jellyfish extract containing the glycoprotein (hereinafter, referred to as "mucin components") need to be subjected in advance to treatment for removal or reduction of endotoxin-containing pathogenic components, antigenic components, and allergenic components.

The combined formulation of the present invention may be composed of separate formulations: a formulation containing a hyaluronic acid; and a formulation containing a mucin component; or it may be composed of a single formulation containing a hyaluronic acid and a mucin component as a mixture. The dosage form of the combined formulation is preferably an injectable formulation that can be directly injected to an affected part such as an articular cartilage-defective part. In this case, a hyaluronic acid and a mucin component may be separately dissolved in appropriate solvents to prepare distinct injectable formulations. Alternatively, the two may be mixed and dissolved in an appropriate solvent to prepare a single injectable formulation. The types of injectable formulation is preferably an aqueous injectable formulation or an aqueous suspension injectable formulation. A solvent to be used herein may be any of physiological saline, buffer, and water for injection that are generally used for injectable formulations. An aqueous injectable formulation or an aqueous suspension injectable formulation is prepared by dissolving or suspending a hyaluronic acid or a mucin component, or both of them in the above solvent while heating as necessary, sterilizing the resultant, filling a container for an injectable formulation with the resultant, and then sealing the container. Further, an injectable formulation may optionally be supplemented with a suspending agent, a stabilizer, a buffering agent, a preservative, an antiseptic, a thickener, a tonicity agent, a water-soluble or water-swelling polymer, a pH adjusting agent, and the like.

When a hyaluronic acid is dissolved in the above solvent to prepare a formulation containing the hyaluronic acid, a concentration that enables easy handling in clinical application may be selected as the concentration of the hyaluronic acid.

For example, the concentration ranges from 0.1% by weight to 5% by weight, and preferably ranges from 0.2% by weight to 2% by weight.

Further, when a mucin component is dissolved in the above solvent to prepare a formulation containing the mucin component, a concentration that enables easy handling in clinical application may be similarly selected as the concentration of the mucin component. For example, the concentration (in terms of the amount of mucin) ranges from 0.001% by weight to 20% by weight, and preferably ranges from 0.01% by weight to 1% by weight.

When a single formulation containing a hyaluronic acid and a mucin component as a mixture is prepared, a hyaluronic acid and a mucin component are separately dissolved in the above solvent(s), and then the resulting solutions are mixed at an appropriate amount ratio (e.g., 1:1) to prepare a formulation. In the finally prepared combined formulation, the content of the hyaluronic acid ranges from 0.1% by weight to 1% by weight and the content of the mucin component ranges from 0.005% by weight to 1% by weight. Mixing is preferably performed via gentle agitation of the mixture for about several hours to some dozen hours.

The dosage of the combined formulation of the present invention may be determined according to clinically employed dosages and can be appropriately selected depending on the age and body weight of the subject, the type and symptoms of the disease, the administration method, the administration period, and so on. For example, in the case of a patient with osteoarthritis (adult, body weight of about 60 kg), a hyaluronic acid and a mucin component are successively administered intraarticularly in an amount ranging from about 5 mg to 100 mg and preferably an amount ranging from about 10 mg to 50 mg per administration weekly. Further, since both the hyaluronic acid and the mucin component in the combined formulation of the present invention are lost via degradation or metabolism within a certain time period, it is preferable to successively administer them several times or more for a certain time period, for example, at intervals of 1 week to 10 days. Since it is generally expected that 10% to 50% of the components (depending on patients) are lost via metabolism within one week, it is recommended to administer them, for example, every other week.

A method for administering the combined formulation of the present invention may be a method for administering a hyaluronic acid and a mucin component substantially at the same time. For example, the above formulation containing a hyaluronic acid and the above formulation containing a mucin component may be administered to a subject completely at the same time or may be administered successively within a short time (preferably within several minutes). To further fully increase the effect, it is preferable to administer a formulation prepared by thoroughly mixing a hyaluronic acid and a mucin component in advance. Therefore, examples of the administration modes of the combined formulation of the present invention include: (a) administration of a single formulation obtained by simultaneously formulating a hyaluronic acid and a mucin component; (b) simultaneous administration, via the same route of administration, of 2 types of formulations obtained by formulating a hyaluronic acid and a mucin component separately; (c) administration, via the same route of administration at different times, of 2 types of formulations obtained by formulating a hyaluronic acid and a mucin component separately (e.g., administration in the order of a hyaluronic acid followed by a mucin component, or administration in the reverse order); (d) simultaneous administration, via different routes of administration, of 2 types of formulations obtained by formulating a hyaluronic acid and a mucin component separately; and (e) administration, via different routes of administration at different times, of 2 types of formulations obtained by formulating a hyaluronic acid and a mucin component separately.

The treatment using the combined formulation of the present invention encompasses both injection treatment and open system treatment such as incisional surgery. Preferably, the administration is performed by local administration. For example, the combined formulation is injected into a joint cavity or synovial fluid of a knee joint, a hip joint, an ankle joint, an elbow joint, a jaw joint, a shoulder joint (shoulder joint cavity, subacromial bursa, and tendon sheath of biceps brachii muscle), or the like which is thought to be damaged.

The thus administered hyaluronic acid and the mucin component in the combined formulation of the present invention cooperatively exert the action of accelerating chondrogenesis, the action of accelerating chondrocyte growth, the action of accelerating chondrocyte differentiation, the action of accelerating cartilage matrix production, and the action of protecting cartilages. Therefore, through administration of the combined formulation of the present invention to mammals (e.g., humans, mice, rats, rabbits, dogs, cats, cattle, horses, pigs, and monkeys), cartilage tissue that is damaged or made defective by a joint disease can be functionally and physiologically repaired and regenerated into an appropriate tissue on the basis of the above actions. The combined formulation of the present invention can be used for treatment of joint diseases, particularly diseases related to degeneration, denaturation, deformation, and other abnormalities of articular cartilage, such as osteoarthritis, rheumatoid arthritis, shoulder periarthritis, and temporomandibular arthrosis, or when regenerative medicine such as chondrocyte transplantation is performed.

The present invention will be further described specifically by referring to Examples. However, the present invention is not limited by such examples.

REFERENCE EXAMPLE

Preparation of Crudely Purified Jellyfish-Derived Mucin

Extracts derived from jellyfish (moon jelly (*Aurelia* sp.) and Nomura's jellyfish (*Nemopilema nomurai*)) to be used in Examples below were prepared by the method as described below. Frozen jellyfish bodies were thawed, and washed with water. Then, solid and liquid were separated from each other using a centrifuge. After removal of the liquid, the remaining solid part was cut into about 5-mm to 1-cm square fragments using a mixer, water was added thereto, and then shaking-extraction was performed at 4° C. Subsequently, the resultant was centrifuged at 10000 g for 15 minutes while keeping the temperature at 4° C., and the supernatant extract was collected to remove the solid content. Three volumes of ethanol was added to the extract while stirring, and then the mixture was allowed to stand in a refrigerator. After the mixture was allowed to stand overnight, it was centrifuged at 10000 g for 15 minutes while keeping the temperature at 4° C. The thus generated gelatinous precipitate was collected and the supernatant was removed. Furthermore, the collected precipitate was dissolved in a small amount of water, and then the solution was centrifuged at 10000 g for 15 minutes while keeping the temperature at 4° C. After centrifugation, the supernatant was separated, purified by dialysis, and then freeze-dried. The resultants were obtained in the form of crudely purified mucins.

Example 1

Confirmation of Changes in Joint Cartilage Via Administration of Animal-Mucin-Type Glycoproteins into Normal Knee Joints and the Presence or the Absence of Inflammation Animal mucin-type glycoproteins were administered into normal knee joints of experimental animals (JW rabbit, 3 kg). As animal mucin-type glycoproteins, the moon jelly-derived mucin (qniumucin) extract and the Nomura's jellyfish-derived mucin (qniumucin) extract obtained in Reference Example above were used. Solutions of the above jellyfish-derived mucin extracts (crudely purified mucins) in physiological saline (concentrations: 0.1 mg/mL; 0.5 mg/mL; and 1.0 mg/mL) were prepared and then administered. To examine short-term effects, blood data (WBC and CRP) were obtained before administration, on day 1 after administration, and on day 4 after administration, and appearance was observed. As shown in Table 1 below, no significant change was observed for either WBC or CRP, and there was no abnormality found in terms of the appearance of knee joints.

TABLE 1

| Blood collection data | | Before administration | After 1 day | After 4 days |
|---|---|---|---|---|
| Moon jelly-derived mucin extract | WBC | 4200-6100 | 4900-6500 | 5100-5700 |
| | CRP | 0.02 or less | 0.02 or less | 0.02 or less |
| Nomura's jellyfish-derived mucin extract | WBC | 5300 | 5700-6700 | 4800 |
| | CRP | 0.02 or less | 0.02 or less | 0.02 or less |

Figure 1:
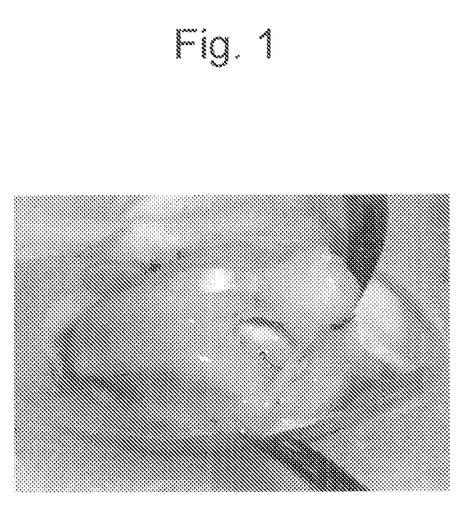
FIG. 1 shows the gross appearance of the cartilage tissue of a normal knee joint to which a mucin-type glycoprotein was administered.
Figure 2:
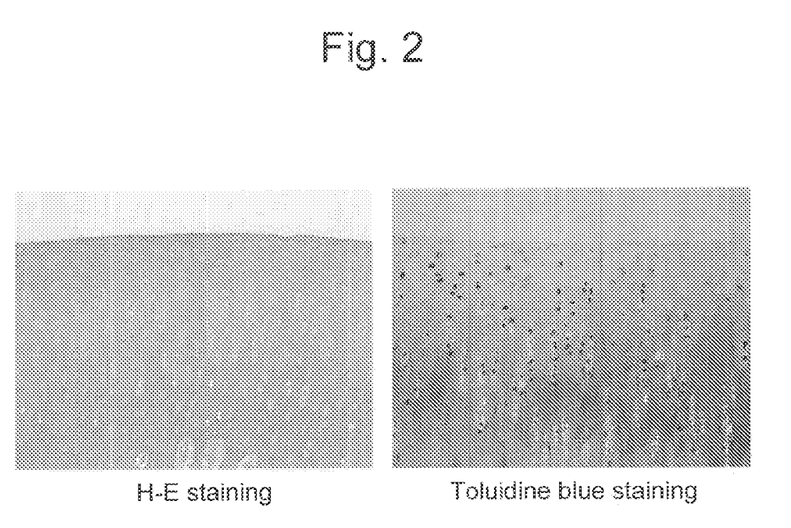
FIG. 2 shows an H-E stain image and a Toluidine-Blue stain image showing the cartilage tissue of a normal knee joint to which a mucin-type glycoprotein was administered.

Further, to examine long-term effects, appearance and intraarticular parts were macroscopically observed after 4 weeks. No change in appearance was noted, intraarticular parts were found to retain no synovial fluid, and articular cartilage was maintained in a normal state. Further, no obvious hyperplasia of synovial membrane was observed (FIG. 1). When articular cartilage was histologically observed via H-E staining and Toluidine-Blue staining, no change was observed in cartilage tissue (FIG. 2).

Example 2

Confirmation of Effects Resulting from the Administration of Combinations of Animal Mucin-Type Glycoproteins and Hyaluronic Acid into Artificially Injured Knee Joints 1. Experimental Materials and Method
(1) Reagent The moon jelly-derived mucin (qniumucin) extract and the Nomura's jellyfish-derived mucin (qniumucin) extract obtained in Reference Example were each dissolved in physiological saline at a concentration of 1 mg/1 mL and then used as animal mucin-type glycoproteins. In addition, the amount of endotoxin in each jellyfish-derived mucin extract (crudely purified mucin) used herein was confirmed to be 10 EU/ml or less in advance by simple measurement using Endosafe-PTS (Endosafe, Charles River Laboratories Japan Inc., Kanagawa, Japan). Further, as a hyaluronic acid, an aqueous hyaluronic acid solution for treatment (Kaken Pharmaceutical Co. Ltd.; Product name: Artz (1 wt %); average molecular weight of hyaluronic acid: about 800,000; concentration: 25 mg/25 mL) was used.

(2) Animals

Japanese white rabbits (female, body weight of 3 kg) were purchased from Tokyo Laboratory Animals Science Co., Ltd. Rabbits were separately housed and reared in cages from FRP (W450×H450×D900 mm).

(3) Osteoarthritis (OA) Model

As an OA model, an anterior cruciate ligament transection (ACL-T) model [Moskowitz R. W. et al., Arthritis Rheum 16, pp. 397-405 (1973); Shapiro, F. Glimcher, M. J., Clin. Orthop. 147, pp. 287-95 (1980); Korkala O. et al., Acta Orthop Scand 55, pp. 273-277 (1984); Messner, K., Clin Biomech 9, pp. 37-43 (1994)] was prepared. Under inhalation anesthesia with isoflurane (Forane, ABBOTT JAPAN Co., LTD., Tokyo, Japan), an about 3-cm medial patellar incision was aseptically made on each knee of rabbits, so as to expose the patella and patellar tendon. Thereafter, the articular capsule was incised through a medial patellar approach. Furthermore, the patella was dislocated laterally while keeping the knee joint in the extension position, the knee joint was then flexed, and the anterior cruciate ligament was transected under direct visualization. Subsequently, the patella was repositioned and then the subcutaneous muscular coat and the skin were separately sutured with nylon thread.

Rabbits subjected to transection of anterior cruciate ligaments at both knee joint were divided into 6 groups at random (Table 2 below). Physiological saline was intraarticularly administered to group A (a control group). Only hyaluronic acid was intraarticularly administered to group B (to which hyaluronic acid was administered alone). A mixture of the Nomura's jellyfish-derived mucin extract and physiological saline was intraarticularly administered to group C1 (to which the Nomura's jellyfish-derived mucin extract was administered alone). A mixture of the moon jelly-derived mucin extract and physiological saline was intraarticularly administered to group C2 (to which the moon jelly-derived mucin extract was administered alone). A mixture of the Nomura's jellyfish-derived mucin extract and hyaluronic acid was intraarticularly administered to group D1 (to which a combination of Nomura's jellyfish-derived mucin extract+hyaluronic acid was administered). A mixture of the moon jelly-derived mucin extract and hyaluronic acid was intraarticularly administered to group D2 (to which a combination of the moon jelly-derived mucin extract+hyaluronic acid was administered). The dosage was 1 ml in total per administration. One (1) ml of physiological saline was administered to group A. A mixture of 0.5 ml of hyaluronic acid and 0.5 ml of physiological saline was administered to group B. A mixture of 0.5 ml of one of the jellyfish-derived mucin extracts and 0.5 ml of physiological saline was administered to groups C1 and C2. A mixture of 0.5 ml of one of the jellyfish-derived mucin extracts and 0.5 ml of hyaluronic acid was administered to groups D1 and D2.

TABLE 2

| Group | Hyaluronic acid (molecular weight: 800,000) | Nomura's jellyfish-derived mucin-containing extract | Moon jelly-derived mucin-containing extract |
|---|---|---|---|
| A | 0 | 0 | 0 |
| B | 5 mg/0.5 wt % | 0 | 0 |
| C1 | 0 | 0.5 mg/0.025 wt % | 0 |
| C2 | 0 | 0 | 0.5 mg/0.025 wt % |
| D1 | 5 mg/0.5 wt % | 0.5 mg/0.025 wt % | 0 |
| D2 | 5 mg/0.5 wt % | 0 | 0.5 mg/0.025 wt % |

Figure 3:
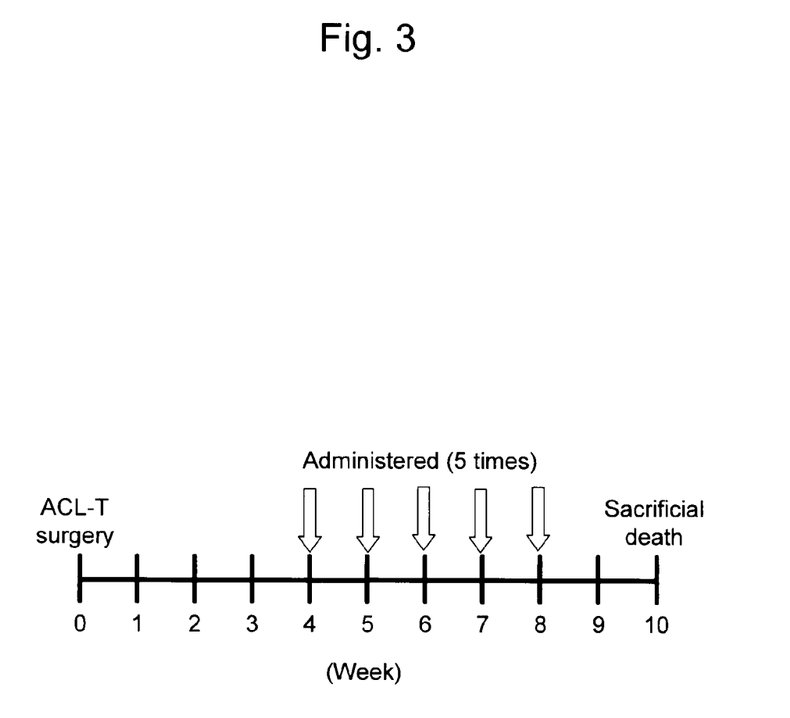
FIG. 3 shows the schedule for administering an agent to an anterior cruciate ligament transection OA model.

After the transection of the anterior cruciate ligament, intraarticular administration was initiated on week 4. Specifically, intraarticular administration was performed 5 times in total, on week 4, week 5, week 6, week 7, and week 8 (FIG. 3). Intraarticular administration was performed via the lateral upper border of a patella of a rabbit knee joint using a 26G needle syringe (TERUMO CORPORATION, Tokyo, Japan) under inhalation anesthesia with isoflurane. Further, on week 10 after the transection of the anterior cruciate ligament, rabbits were sacrificed using pentobarbital salt (Nembutal, Dainippon Sumitomo Pharma Co., Ltd. Osaka, Japan).

(4) Macroscopic Evaluation and Histological Evaluation of Articular Cartilages

On week 10 after surgery, femoral condyles of knee joints were observed immediately after the sacrifice of rabbits. After the sacrifice of each rabbit, both femoral condyles of knee joints were excised and then fixed with a 4% neutral buffered formalin fixative (pH7.4). The fixed sample was demineralized with 10% ethylenediamine tetraacetic acid (EDTA) (pH7.4) and then paraffin-embedded. Paraffin sections were prepared in the sagittal plane of the femoral condyle, followed by safranin-O staining.

The histopathological evaluation of cartilage degeneration was performed using Osteoarthritis cartilage histopathology: grading and staging [Pritzker, K. P. et al., Osteoarthritis Cartilage. 14, pp. 13-29 (2006)]. Evaluation was numerically expressed based on the OA scores calculated according to the following formula.

OA score (1-24)=site with the highest degree of cartilage degeneration (grades 1-6)×degeneration area (stages 1-4)

2. Results (1) Gross Appearance

Figure 4:
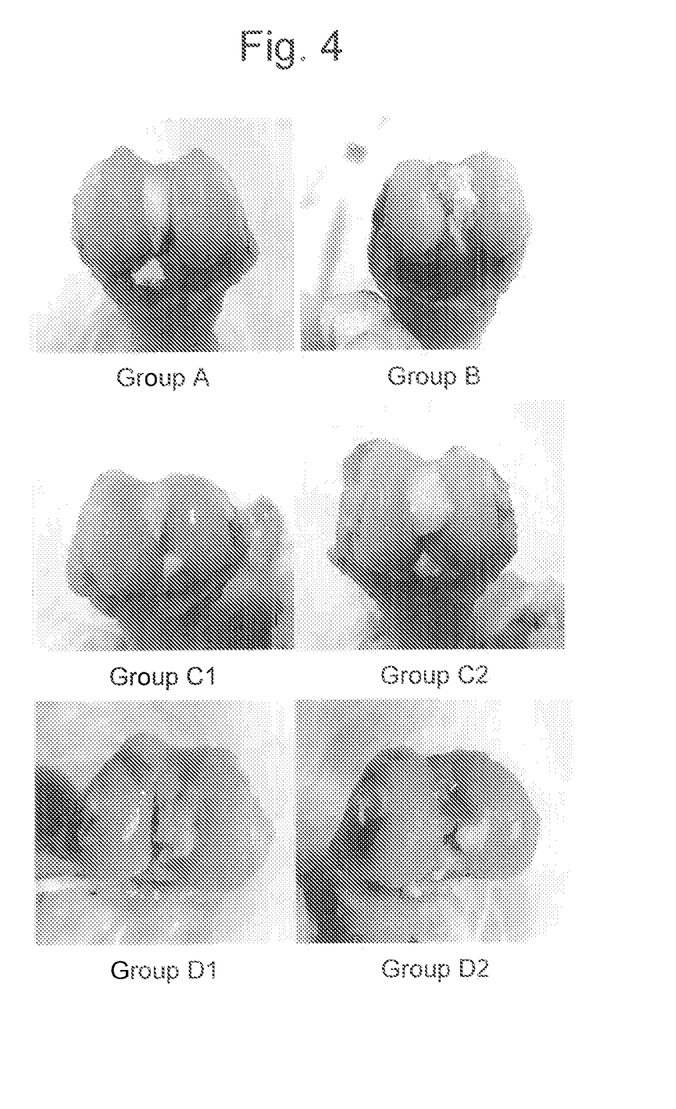
FIG. 4 shows gross appearance showing the femoral condyles of knee joints of an anterior cruciate ligament transection OA model (week 10 after surgery) to which predetermined agents were administered (group A: the physiological saline (control) group; group B: the group to which a hyaluronic acid was administered alone; group C1: the group to which Nomura's jellyfish (*Nemopilema nomurai*)-derived mucin extract was administered alone; group C2: the group to which a moon jelly (*Aurelia* sp.)-derived mucin extract was administered alone; group D1: the group to which a combination of Nomura's jellyfish-derived mucin extract+a hyaluronic acid was administered; and group D2: the group to which a combination of moon jelly-derived mucin extract+a hyaluronic acid was administered).

FIG. 4 shows the results of macroscopic observation of group A, group B, group C1, group C2, group D1, and group D2. In group A, severe medial and lateral cartilage defects reaching subchondral bone were observed. The defects were found to reach subchondral bone, affecting the entire weight-bearing area. In group B, the medial and lateral cartilage surfaces were irregular, and some cartilage defects reaching subchondral bone were observed. In groups C1 and C2, similarly to group A, the medial and lateral cartilage defects reaching subchondral bone were observed, but no difference was found in terms of defected areas. In group D, the medial cartilage surfaces were irregular, no exposure of subchondral bone was observed, and only few affected areas were found. When group D (a combination of hyaluronic acid and mucin) was compared with group B (hyaluronic acid alone), cartilage defects in group D were found to be slight as compared with group B. Differences depending on the types of jellyfish were not observed in both groups C and D.

(2) Histological Examination

Figure 5:
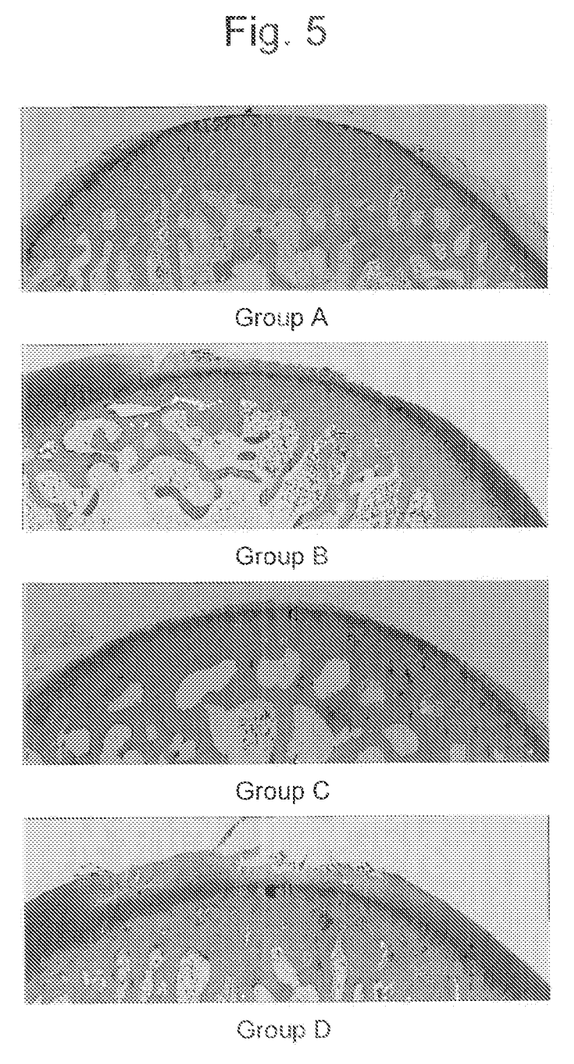
FIG. 5 shows safranin-O stain images showing the femoral condyles of knee joints in an anterior cruciate ligament transection OA model (week 10 after surgery) to which predetermined agents were administered (group A: the physiological saline (control) group; group B: the group to which a hyaluronic acid was administered alone; group C: the group to which a jellyfish-derived mucin extract was administered alone; group D: the group to which a combination of jellyfish-derived mucin extract+a hyaluronic acid was administered).

FIG. 5 shows the safranin-O stain images of group A, group B, group C, and group D. In group A, exposure of subchondral bone was observed and cartilage defects were found to reach subchondral bone. In group B, cartilage fissures reached deep layers, and reduction in staining was observed for the layer above the tide mark. The cell arrangements were not retained and decreases in cells were also observed. In group C, cartilage layers were found to slightly remain, but were not stained, and chondrocytes disappeared. In group D, stripping of cartilage layers was observed, but a fissure was found to reach the intermediate layer in most cases. Fissures in group D were found to be clearly shallower than those of group B. Cell arrangements were found to be relatively retained and the degree of reduction in staining was found to be milder than group B. Differences depending on the types of jellyfish were not observed similarly to gross appearance.

Figure 6:
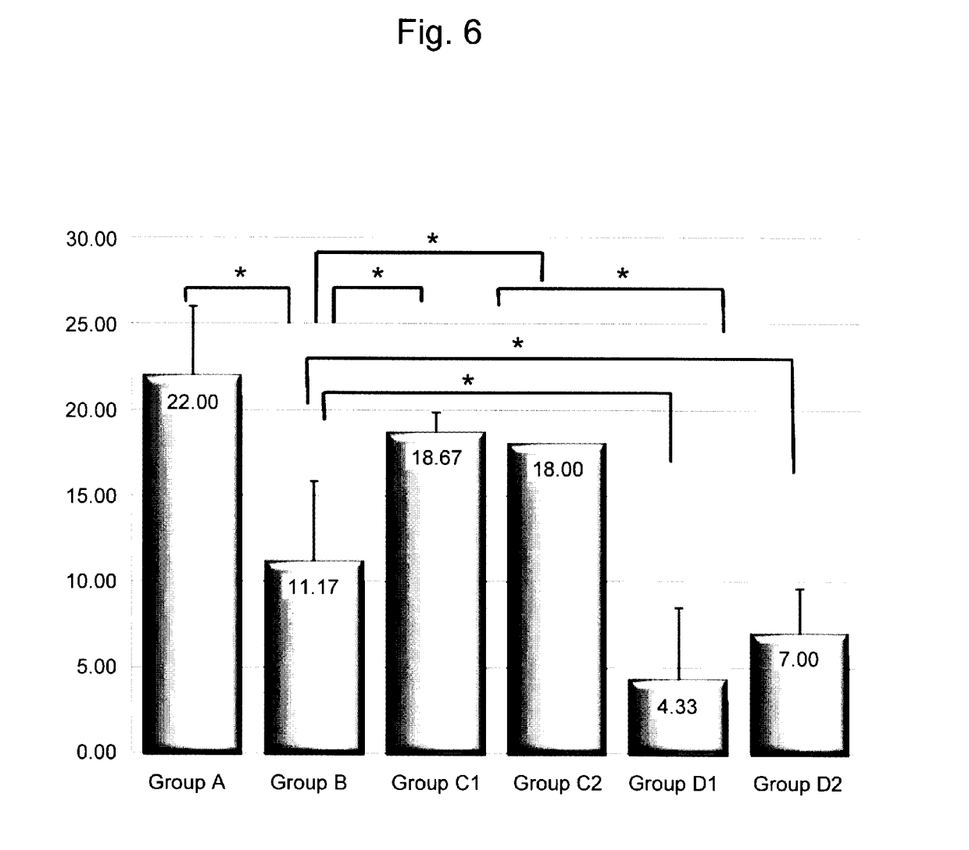

FIG. 6 shows average OA scores representing the degrees of cartilage degeneration for group A, group B, group C1, group C2, group D1, and group D2. The average OA scores were: 22.00±4.00 for group A; 11.17±4.65 for group B; 18.67±1.15 for group C1; 18.00±0.00 for group C2; 4.33±4.16 for group D1; and 7.00+2.65 for group D2. No significant difference was found between group A and group C, but significant differences (*: P<0.05) were observed between groups A and C and group B, between group B and group D, and between group C and group D. Differences depending on the types of jellyfish were not observed in both groups C and D.

All publications, patents, and patent applications cited herein are incorporated herein by reference in their entirety.

INDUSTRIAL APPLICABILITY

The present invention can be used in the field of medicine manufacturing for treatment and alleviation of joint diseases and articular cartilage regeneration.

The invention claimed is:

1. A method for treating joint diseases, comprising injecting a hyaluronic acid and an animal mucin-type glycoprotein in combination into a joint cavity or into synovial fluid of a subject suffering from a joint disease, wherein 95% or more of the full-length amino acid sequence of the animal mucin-type glycoprotein is composed of a mucin region, and wherein the animal mucin-type glycoprotein has a repeat structure that comprises 3 to 2000 repeating units, wherein each repeating unit consists of the amino acid sequence represented by the following formula (I) (SEQ ID NO: 1):

Val-Xaa-Glu-Thr-Thr-Ala-Ala-Pro     (I)

wherein Xaa denotes Val or Ile; and sugar chains are bound to 50% or more of all Thr residues in the repeat structure.

2. The method according to claim 1, wherein the animal mucin-type glycoprotein is extracted from jellyfish.

3. The method according to claim 1, wherein the treatment of joint diseases is the repair and regeneration of articular cartilage.

4. The method according to claim 1, wherein 98% or more of the full-length amino acid sequence of the animal mucin-type glycoprotein is composed of a mucin region.

5. The method according to claim 1, wherein 100% of the full-length amino acid sequence of the animal mucin-type glycoprotein is composed of a mucin region.

6. The method according to claim 1, wherein sugar chains are bound to 70% or more of all Thr residues in the repeat structure.

7. The method according to claim 1, wherein sugar chains are bound to 80% or more of all Thr residues in the repeat structure.

8. The method according to claim 1, wherein the hyaluronic acid and the animal mucin-type glycoprotein are injected simultaneously, separately, or sequentially.

9. The method according to claim 1, wherein the hyaluronic acid and the animal mucin-type glycoprotein are injected as separate formulations, wherein a hyaluronic acid formulation comprises 0.1 to 5 wt % of the hyaluronic acid, and a mucin formulation comprises 0.001 to 20 wt % of the animal mucin-type glycoprotein.

10. The method according to claim 1, wherein the hyaluronic acid and the animal mucin-type glycoprotein are injected as a single formulation, wherein the single formulation comprises 0.1 to 1 wt % of the hyaluronic acid, and 0.005 to 1 wt % of the animal mucin-type glycoprotein.

* * * * *